United States Patent
Richardson (10) Patent No.: US 10,028,836 B2
(45) Date of Patent: Jul. 24, 2018

(54) SYSTEM AND METHOD OF OSTEODISTRACTION

(71) Applicant: The Regents of the University of Colorado, Denver, CO (US)

(72) Inventor: Marlin D. Richardson, Denver, CO (US)

(73) Assignee: The Regents of the University of Colorado, Denver, CO (US)

(*) Notice: Subject to any disclaimer, the term of this patent is extended or adjusted under 35 U.S.C. 154(b) by 0 days.

(21) Appl. No.: 15/415,013

(22) Filed: Jan. 25, 2017

(65) Prior Publication Data

US 2017/0209273 A1 Jul. 27, 2017

Related U.S. Application Data

(60) Provisional application No. 62/287,235, filed on Jan. 26, 2016.

(51) Int. Cl.

| | |
|---|---|
| *A61F 2/44* | (2006.01) |
| *A61B 17/88* | (2006.01) |
| *A61F 2/28* | (2006.01) |
| *A61B 17/70* | (2006.01) |
| *A61B 17/56* | (2006.01) |
| *A61B 17/68* | (2006.01) |

(Continued)

(52) U.S. Cl.
CPC ............ *A61F 2/28* (2013.01); *A61B 17/7059* (2013.01); *A61B 17/88* (2013.01); *A61B 17/8858* (2013.01); *A61F 2/2846* (2013.01); *A61B 2017/564* (2013.01); *A61B 2017/681* (2013.01); *A61F 2/44* (2013.01); *A61F 2/4611* (2013.01); *A61F 2/4684* (2013.01); *A61F 2002/30545* (2013.01)

(58) Field of Classification Search
CPC .. A61F 2/28; A61F 2/2846; A61F 2/44; A61F 2/4611; A61F 2/4684; A61F 2002/30545; A61B 17/7059; A61B 17/88; A61B 17/8858; A61B 2017/564; A61B 2017/681
USPC ........... 606/280, 281, 286, 308, 90, 99, 105, 606/86 A, 86 B; 623/17.11, 17.16
See application file for complete search history.

(56) References Cited

U.S. PATENT DOCUMENTS

| | | | | |
|---|---|---|---|---|
| 4,263,914 A | * | 4/1981 | Pawlak ................. | A61H 21/00 601/112 |
| 5,593,409 A | * | 1/1997 | Michelson ......... | A61B 17/1671 606/247 |

(Continued)

OTHER PUBLICATIONS

7pcs Drill Bit Stop Collars Set Exact Hole Depth Bits Locator Drill Clamp Metric 3mm 4mm 5mm 6mm 8mm 10mm 12mm + Ipc Hex Wrench; http://www.amazon.com/Drill-Collars-Locator-Metric-Wrench/dp/B00UN1NKHQ.

*Primary Examiner* — Pedro Philogene
*Assistant Examiner* — David C Comstock
(74) *Attorney, Agent, or Firm* — Snell & Wilmer L.L.P.

(57) ABSTRACT

Systems, devices, and methods for osteodistraction are provided. The systems and devices comprise ellipsoidal cams for providing controlled distraction of adjacent bone structures using a rotational force to produce displacement of the bone structures. An implantable distraction cam system is provided, along with instruments for achieving progressive osteodistraction with reduced risk to a patient.

17 Claims, 7 Drawing Sheets

(51) Int. Cl.
 A61F 2/30 (2006.01)
 A61F 2/46 (2006.01)

(56) References Cited

U.S. PATENT DOCUMENTS

| | | | | |
|---|---|---|---|---|
| 5,716,415 | A * | 2/1998 | Steffee | A61F 2/447 623/17.16 |
| 5,893,890 | A * | 4/1999 | Pisharodi | A61B 17/025 606/247 |
| 6,290,724 | B1 * | 9/2001 | Marino | A61F 2/4455 623/17.11 |
| 6,309,421 | B1 * | 10/2001 | Pisharodi | A61B 17/025 606/247 |
| 6,368,325 | B1 * | 4/2002 | McKinley | A61F 2/4455 606/99 |
| 6,527,773 | B1 * | 3/2003 | Lin | A61F 2/446 606/247 |
| 8,449,580 | B2 | 5/2013 | Voellmicke et al. | |
| 8,915,946 | B2 | 12/2014 | Khanna | |
| 9,107,708 | B2 | 8/2015 | Robinson | |
| 2007/0270965 | A1 * | 11/2007 | Ferguson | A61B 17/7059 623/17.11 |
| 2008/0319550 | A1 * | 12/2008 | Altarac | A61B 17/7065 623/17.16 |
| 2013/0211524 | A1 | 8/2013 | Hughes | |
| 2014/0067065 | A1 | 3/2014 | Shepard et al. | |
| 2014/0135845 | A1 | 5/2014 | Null et al. | |

\* cited by examiner

SYSTEM AND METHOD OF OSTEODISTRACTION

CROSS-REFERENCE TO RELATED APPLICATIONS

This application is a nonprovisional of, claims priority to and the benefit of, U.S. Application Ser. No. 62/287,235 filed Jan. 26, 2016 and entitled "SYSTEM AND METHOD OF OSTEODISTRACTION," and is hereby incorporated by reference in its entirety.

FIELD

The present disclosure relates to systems and methods of distracting adjacent bone tissue, and more specifically, systems and methods for predictably and progressively increasing a dimension of distraction between two bone tissue surfaces while reducing the risk of slippage or an abrupt return of a bone to its native position, thereby reducing the risks associated with various surgical procedures.

BACKGROUND

Figure 1A:
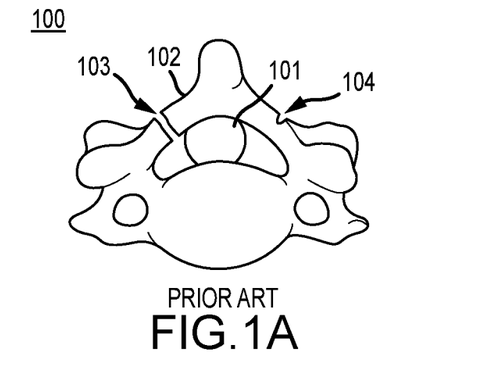
FIGS. 1A-1C illustrate a cervical vertebra in various stages of a prior art distraction and implant placement procedure.
Figure 1B:
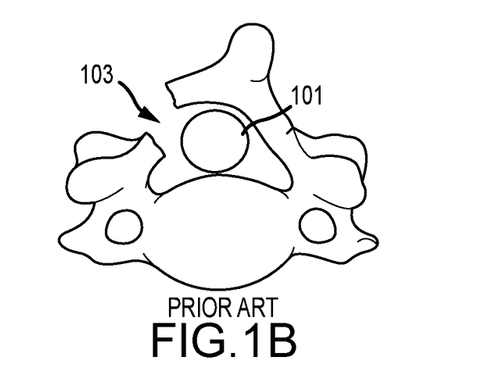
Figure 1C:
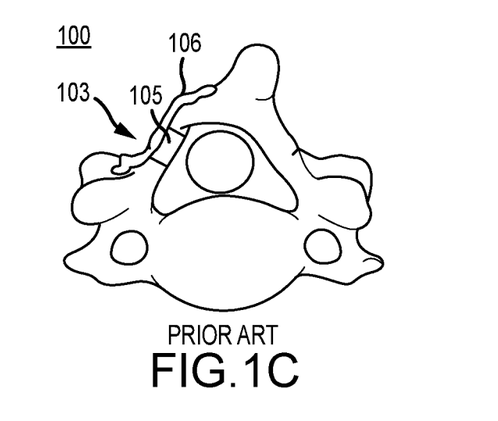

Various surgical procedures require the distraction of two bones or other hard anatomical features. For example, a cervical laminoplasty procedure requires distraction of the lamina of the spine away from the lateral mass of the vertebra. FIGS. 1A-1C illustrate a cervical vertebra in various stages of a cervical laminoplasty procedure. With reference to FIG. 1A, a vertebra 100 with a compression of spinal cord 101. A distraction of the lamina is frequently initiated by cutting lamina 102 on one side of the vertebra to create a gap 103 in the lamina. An incomplete kerf 104 on the contralateral lamina may serve as a hinge. Distraction of the lamina increases the dimension of the gap 103, thereby elevating the lamina and opening the spinal canal, as shown in FIG. 1B. Distraction of the lamina can relieve spinal stenosis and pressure on the spinal cord 101 or surrounding nerve roots. As shown in FIG. 1C, an implant 105 may be placed in the enlarged laminar gap 103 following distraction and secured to the vertebra 100 using a plate 106.

Figure 2A:
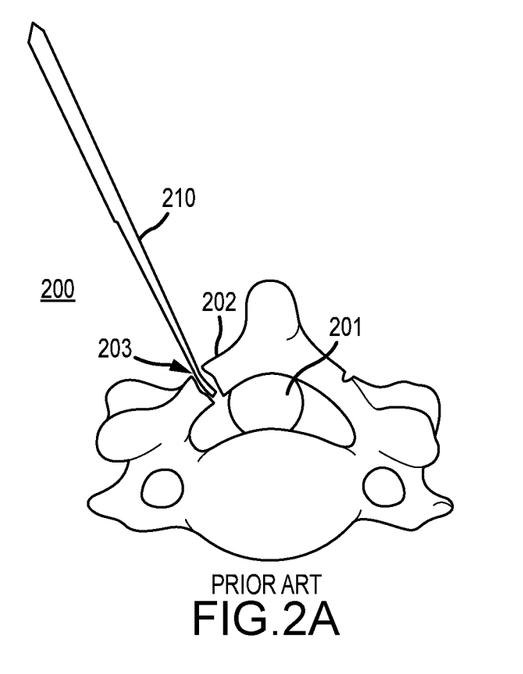
FIGS. 2A and 2B illustrate a cervical vertebra in various stages of a prior art distraction procedure.
Figure 2B:
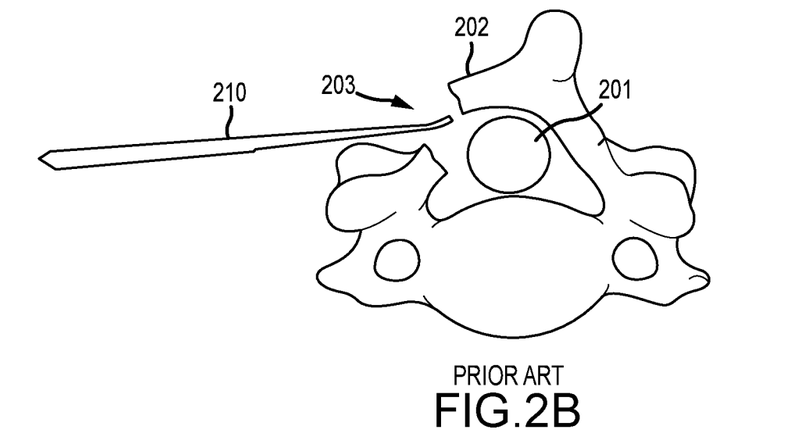

An osteodistraction procedure can present risks to a patient. In a cervical laminoplasty, various common approaches to engaging and distracting the lamina present risks to the patient. The instruments that may be used, the force vectors and movements applied to the lamina using the instruments, and the manner in which they engage the surfaces of the bones involve risks of over-insertion and slippage, which can lead to direct and/or indirect trauma to the spinal cord. For example and as illustrated in FIGS. 2A and 2B, a curet 210 may be used to distract lamina 202 of vertebra 200. Curet 210 may first be inserted into laminar gap 203 (FIG. 2A). Such insertion involves directing curet 210 with force toward spinal cord 201, with a risk of overinsertion of curet 210 and injury to the spinal cord. Following insertion of curet 210 into laminar gap 203, curet 210 can be used to distract lamina 202, such as with a prying or lifting movement (FIG. 2B). Distraction using this or similar instruments and techniques presents a risk that lamina 202 will slip from the distraction instrument and return to its original position abruptly or forcefully and in an uncontrolled manner, causing injury to spinal cord 201.

The present disclosure provides systems and methods of osteodistraction that provide more predictable and/controllable distraction of two bone structures, thereby decreasing the risks to the patient associated with osteodistraction procedures.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

DETAILED DESCRIPTION

The detailed description of exemplary embodiments herein makes reference to the accompanying drawings, which show exemplary embodiments by way of illustration and their best mode. While these exemplary embodiments are described in sufficient detail to enable those skilled in the art to practice the inventions, it should be understood that other embodiments may be realized and that logical, chemical, and mechanical changes may be made without departing from the spirit and scope of the inventions. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

As used herein, the terms "proximal" and "distal" refer to portions of a tool or device located nearer to and further from an operator, respectively.

As used herein, the term "ellipsoidal" means having at least a portion of the form of an ellipse, including a generally oblong shape partially defined by one or more convexly curved boundary profile segments. As used herein, an object can have an "ellipsoidal" cross-section, notwithstanding that the boundary profile of that cross-section may include non-ellipsoidal features, such as indentations (e.g., a notch or concave boundary profile segment), straight lines, or other boundary profile segment features or irregularities.

Figure 3A:
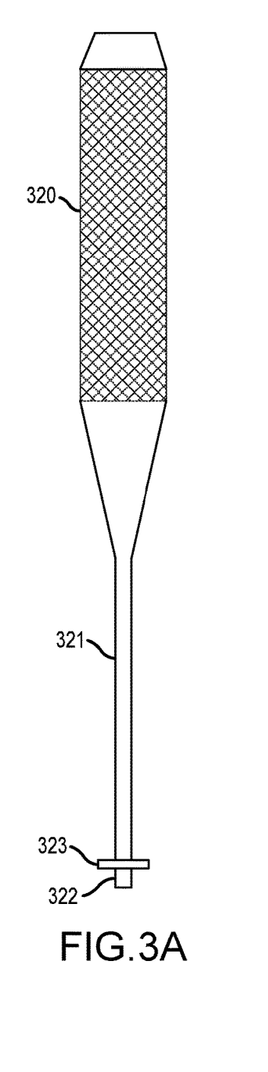
FIGS. 3A-3C illustrate views of a distraction driver in accordance with various embodiments.
Figure 3B:
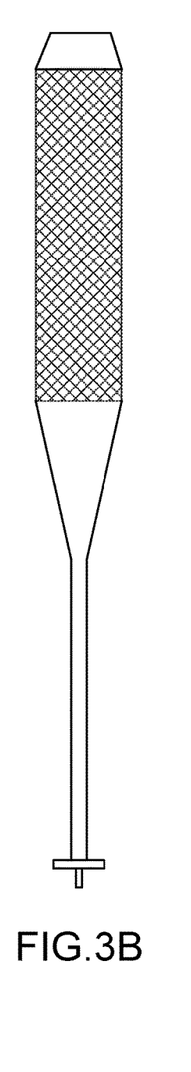
Figure 3C:
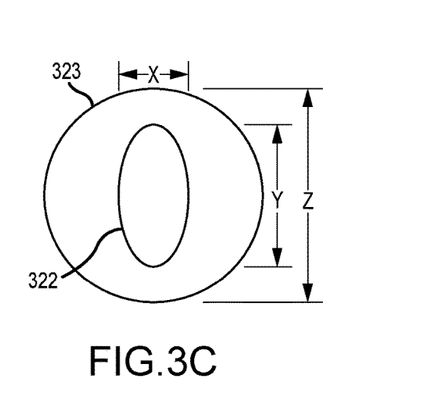

In various embodiments, a kit for performing an osteo-distraction can comprise a distraction driver. With reference now to FIGS. 3A-3C, various views of a distraction driver 300 are illustrated. A distraction driver can comprise an elongated instrument with handle 320 at a proximal end. A shaft 321 may extend distally from the handle, and the shaft may terminate in a cam 322 at the distal end of distraction driver 300. Distraction driver 300 can further comprise a protective plate 323 located proximally to cam 322. With reference specifically to FIG. 3C, a view of the distal end of distraction driver 300 is shown to illustrate the configuration and relative dimensions of cam 322 and protective plate 323 in accordance with various embodiments. As illustrated, cam 322 can comprise an ellipsoidal cross-section or profile having an insertion dimension x and a distraction dimension y that is greater than insertion dimension x. Protective plate 323 can comprise a diameter z that is greater than the distraction dimension y and configured to prevent over-insertion of distraction driver 300 into a gap between two adjacent bone or other structures, such as a laminar gap, kerf or trough.

The cam of a distraction driver such as distraction driver 300 can have any of a range of possible insertion dimensions and distraction dimensions. For example, in various embodiments, insertion dimension x of cam 322 can be any dimension in the range of from about 1 mm to about 20 mm, such as about 1 mm, 2 mm, 3 mm, 4 mm, 5 mm, 6 mm, and so forth, up to about 20 mm, or any other dimension with a non-integer value therebetween. Similarly, distraction dimension y of cam 322 can be any dimension in the range of from about 2 mm to about 30 mm, such as about 2 mm, 3 mm, 4 mm, 5 mm, 6 mm, and so forth, up to about 30 mm, or any other dimension with a non-integer value therebetween, provided that distraction dimension y is greater than insertion dimension x.

Similarly, the cam of a distraction driver can be configured with any suitable cam depth dimension. The depth dimension of a cam is the distance from the distal surface of protective plate 323 to the distal end of cam 322. In various embodiments, the depth dimension of cam 322 can be any suitable dimension to permit the radial walls of cam 322 to engage adjacent bone structures in use without extending into a gap between two bone structures, such as a laminar gap. For example, the depth of a cam may be any dimension in a range of from about 4 mm to about 15 mm.

The protective plate of a distraction driver may be configured with a circular, ellipsoid, or other rounded shape cross-section or profile. For example, protective plate 323 of distraction driver 300 can be configured with a substantially circular profile having a diameter dimension z. In accordance with various embodiments, diameter dimension z is greater than distraction dimension y so that protective plate 323 extends radially from shaft 321 beyond the radial profile of cam 322. In various embodiments, diameter dimension z can range from about 4 mm to about 14 mm, dependent on the insertion dimension x and the distraction dimension y of cam 322. For example, protective plate 323 may be configured with a diameter dimension z that extends radially about 1 mm beyond cam 322 on each side in the distraction dimension axis. In this manner, protective plate 323 may provide a positive stop for insertion of cam 322 in an axial direction into gap between adjacent bone or other structures that may provide a clearance fit for cam 322 in either the insertion dimension x orientation or the distraction dimension y orientation. Any dimension of protective plate 323 diameter dimension z suitable to provide a positive stop relative to the dimensions of cam 322 may be used.

A distraction driver can be manufactured from any material suitable for surgical instrumentation, such as titanium, stainless steel, tungsten carbide, or other suitable materials. A distraction driver can be manufactured as a unitary device, or a distraction driver can be assembled from separate components, such as by joining a separate handle, shaft, protective plate, and/or cam.

In various embodiments, the ellipsoidal cross-sectional profile of cam 322 may be configured to facilitate conversion of rotational motion of distraction driver 300 about the long axis of the driver into substantially linear displacement of two adjacent bone structures between which cam 322 is inserted, thereby increasing the dimension of a gap from a dimension approximating the insertion dimension x of cam 322 to a dimension approximating the distraction dimension y of cam 322. In operation, cam 322 of distraction driver 300 may be inserted into a gap between two adjacent bone structures. The cam may be inserted until the distal surface of protective plate 323 comes into contact with an opposing surface of one or more bone structures. The dimension of the gap may provide a clearance fit for cam 322 in the insertion dimension orientation. Rotation of the driver 300 causes the walls of cam 322 to slide smoothly at the points of contact with the surrounding bone structures on either side of the gap, while the cross-sectional profile of cam 322 functions as a disc-cam, converting the rotational motion of the cam to linear motion of the adjacent bone structures in a direction substantially perpendicular to the axis of distraction driver 300.

In this manner, distraction of the adjacent bone structures can be achieved while substantially reducing the forces directed along a vector oriented toward potentially sensitive, underlying tissue and the attendant risk of instrument slippage and intrusion into such tissue. For example, in a cervical laminoplasty, distraction of the lamina using distraction driver 300 as described above produces linear distraction of the lamina in a direction substantially parallel with the axis of the lamina, without relying on a prying action and instrument force vectors that intersect with the spinal cord, such as those involved in the prior art process illustrated in FIG. 2B. Moreover, distraction is achieved in a controlled manner, with cam 322 of distraction driver 300 contacting surfaces of both adjacent bone structures and occupying the gap between the adjacent bone structures throughout the distraction. This approach substantially reduces the risk associated with slippage of a distraction instruments and procedures that rely on instrument contact with the bone structure on only one side of the gap and/or do not occupy the gap between the adjacent bone structures. Using distraction driver 300, the distraction force can be released in a controlled manner by either reversing the rotation of driver 300, or by advancing rotation of driver 300 if rotation during distraction had proceeded to the point of maximal distraction with the dimension of the gap approximating the distraction dimension y of cam 322.

In various embodiments, a plurality of distractions drivers comprising cams having a range of different insertion dimensions, distraction dimensions, and cam depth dimensions may be provided in various permutations. In this manner, a distraction driver may be operator-selectable based on the particular application, such as the particular distraction procedure to be performed, variations in patient anatomy, and/or accommodation of different desired surgical procedure outcomes and associated sets of surgical instruments or implants. Operator-selection of a distraction driver having a cam depth less than the dimension of the bone structures defining a gap to be distracted affords a further safety feature of the distraction driver device disclosed herein, with the radial dimension of protective plate 323 extending beyond the radial dimensions of cam 322 providing a positive stop for insertion of cam 322 into a gap having a clearance fit for the cam. The positive stop provided by protective plate 323 can thereby serve to prevent over-insertion of a distraction driver having an appropriately selected cam dimensions.

In various embodiments, a kit for performing an osteodistraction can comprise a plurality of distraction drivers. A plurality of distraction drivers can comprise, for example, 2, 3, 4, 5, or more distraction drivers having complementary cam dimensions suitable to provide progressively increasing distraction dimensions y. For example, a kit in accordance with various embodiments can comprise 3 distraction drivers providing distraction dimensions of 4 mm, 6 mm, and 8 mm, thereby providing a distraction dimension delta of about 4 mm between the largest and the smallest distraction driver. The insertion dimensions of the drivers in a kit may be the same. In other embodiments, the insertion dimensions of the drivers in a kit may increase in size in various embodiments. For example, the insertion dimensions of the kit described above could be 2 mm, 3 mm, and 4 mm, respectively, to provide progressively increasing insertion dimensions configured to be compatible with the progressively increased distraction achieved with each distraction driver in the kit. In various embodiments, a kit can comprise any number of distraction drivers having any suitable combination of insertion dimension and distraction dimension, including kits in which each distraction driver has the same insertion dimension but progressively greater distraction dimensions.

Figure 4A:
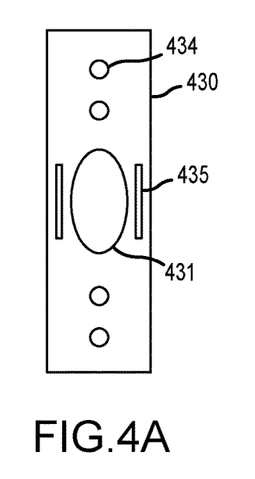
FIGS. 4A-4E illustrate views of a distraction component and a fixation component of a modular system for osteodistraction in accordance with various embodiments.
Figure 4B:
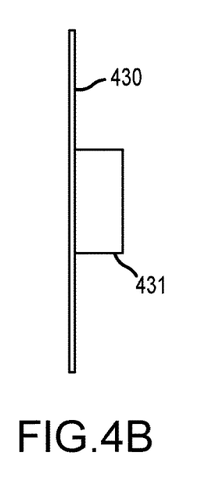
Figure 4C:
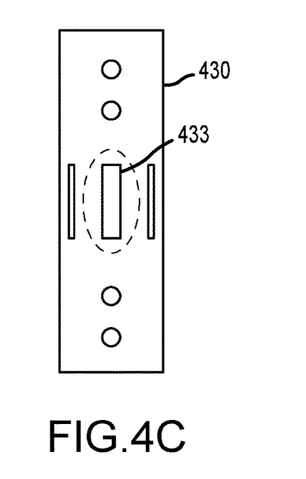
Figure 4D:
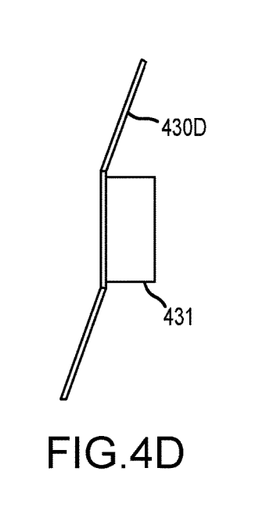
Figure 4E:
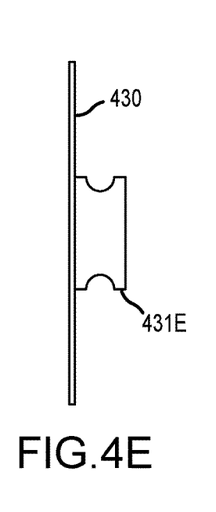
Figure 5:
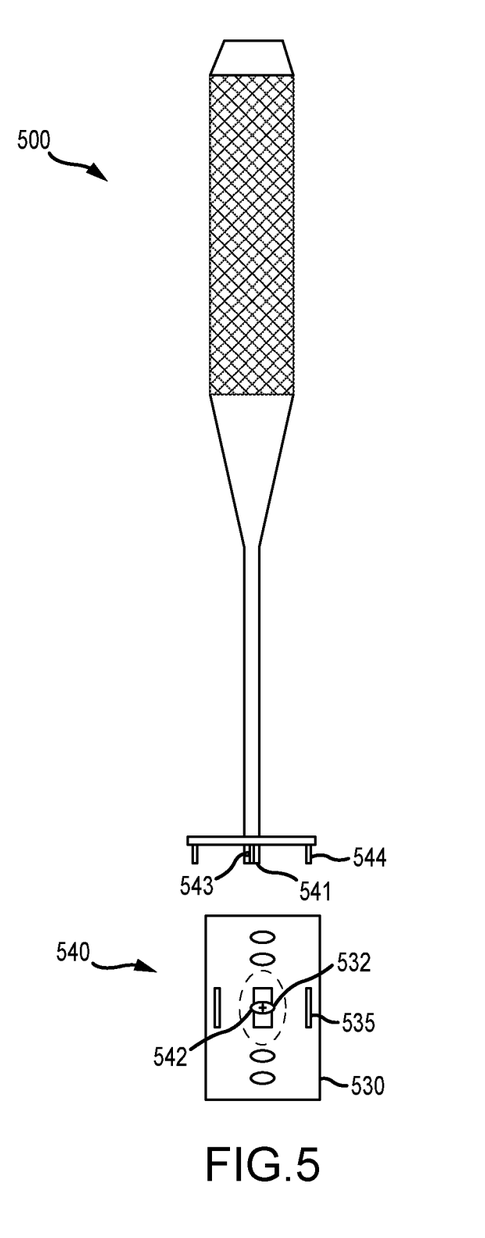
FIG. 5 illustrates a modular system for osteodistraction in accordance with various embodiments of the present disclosure.

In various embodiments, a kit for performing an osteodistraction can comprise an implantable distractor cam device. An implantable distractor cam device can comprise a modular system for osteodistraction that is further comprised of separate, operator-selectable and operator-assembled components. With reference now to FIGS. 4A-4E, an implantable distractor cam device 400 is illustrated. In various embodiments, modular implantable distractor cam device 400 can comprise a distraction component such as distractor cam 431, a fixation component such as fixation plate 430, and an attachment component such as attachment device 532 (FIG. 5). The fixation plate may be configured to be adjustably coupled to the distractor cam using the attachment device to produce an assembled implantable distractor cam device 400.

In various embodiments, a distractor cam 431 can have a configuration similar to that described above with respect to cam 322 of distraction driver 300 (FIGS. 3A-3C). For example, in various embodiments, a distractor cam can have an ellipsoid, disc-cam shape. The distractor cam may be substantially symmetrical about one of an axis in the first dimension and an axis in the second dimension of the ellipsoid shape. Other configurations of a distractor cam are possible. In various embodiments, a distractor cam can comprise features that facilitate stable engagement of the distractor cam comprising a component of the implantable distractor cam device 400 with the adjacent bone structures at the site of implantation. For example and as illustrated in FIG. 4E, distractor cam 431E comprises grooves located near the ends of ellipsoid shape that may more positively engage adjacent bone structures when implanted. Any of another of other surface configurations or features are possible and may be used in a distractor cam in accordance with the present disclosure.

In various embodiments, distractor cam 431 can comprise an implantable material, such as an allograft material comprising human cortical bone and/or cancellous bone. Other implantable materials can be used, such as metals including titanium and stainless steel, polymers including polyetheretherketone (PEEK), polyactic acid, and polyglycolic acid, ceramic materials including aluminum oxide and hydroxyapatite, and other biocompatible materials.

Pre-distraction, for example, using the distraction drivers described above, facilitates achieving final distraction with an implantable distractor cam device 400 having an implantable distractor cam 431 comprising a relatively soft allograft, PEEK, titanium, stainless steel, ceramic, or other implantable material. In addition, performing final distraction with an implantable distractor cam device 400 may provide for enhanced efficiency of an osteodistraction and implant placement procedure such as a laminoplasty by providing for simultaneous distraction and implantation of implantable device 400, as compared to achieving the desired distraction with other instruments followed by placement of an implant in the distracted gap. Moreover, fixation plate 430 can serve a similar function to protective plate 323 of distraction driver 300, with fixation plate 430 having an oversized configuration relative to the cross section of distractor cam 431 suitable to prevent overinsertion of distractor cam 431 into the gap between adjacent bone structures.

In various embodiments, an implantable distractor cam device can comprise a fixation component such as fixation plate 430. A fixation plate can be configured to approximate the contours of a distracted anatomical structure, as illustrated and described below with respect to fixation plate 430D. An implantable distraction cam device can also comprise an attachment component such as attachment device 532 (FIG. 5). Attachment device 532 can comprise, for example, a screw that threadedly engages the distraction cam, such as by driving a self-drilling screw into an allograft distraction cam or a bolt configured to engage a pre-threaded plate or insert in the distraction cam. In various embodiments, fixation plate 430 can be configured to be adjustably coupled to distractor cam 431. For example, a fixation plate can comprise a slot 433 through which attachment device 532 may be inserted, with slot 433 providing for slidable adjustment of the relative position of cam 431 and fixation plate 430. Other attachment components, fastening mechanisms, and adjustable coupling configurations are possible and within the scope of the present disclosure. Tightening or otherwise securing attachment device 532 can secure cam 431 to fixation plate 430. Fixation plate 430 can also comprise surface features such as teeth or protrusions that provide for a positive engagement between the adjacent surfaces of fixation plate 430 and cam 431. Attachment device 532 may be configured to engage fixation plate 430 in a manner that prevents over-engagement or stripping of the distraction cam by the attachment device, such by a distal screw head that positively engages the corresponding surface of the fixation plate. In various embodiments, implantable distractor cam device 400 can comprise features that facilitate engagement of an implantation driver, such as implantation driver slots 435, described in more detail below.

In various embodiments, fixation plate 430 can further comprise fixation apertures 434. Fixation apertures 434 can be used to secure fixation plate 430 to the adjacent bone structures following placement of implantable distractor cam device 400, such as by inserting screws through fixation apertures 434 into the underlying adjacent bone structures.

The modular configuration of implantable distractor cam device 400 can permit selection and attachment of a suitably configured fixation plate to a selected distractor cam 431. For example, a fixation plate may have a planar profile, such as that shown for fixation plate 430 in FIG. 4B, or a fixation plate may be pre-bent to conform to the features of the implantation site, such as fixation plate 430D shown in FIG. 4D. Likewise, fixation plates may have a range of possible lengths and widths to further enhance an operator's ability to obtain an optical configuration of an implantable distractor cam device.

Figure 6:
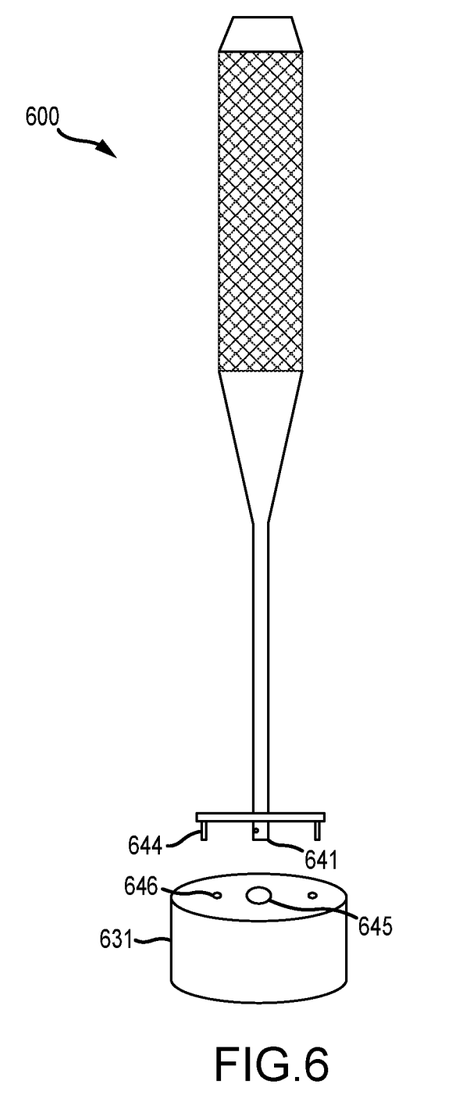
FIG. 6 illustrates a distraction component and an insertion component of a modular system for osteodistraction in accordance with various embodiments of the present disclosure.

In various embodiments and with reference now to FIGS. 5 and 6, a kit for performing an osteodistraction can comprise an insertion component such as implantation drivers 500 and 600. An implantation driver can comprise an elongated shaft with a handle at the proximal end. The distal end of the implantation driver can be configured to securely and reversible engage one of an assembled implantable distractor cam device or a distractor cam. Implantation driver 500 can be configured to engage assembled distractor cam device 540. Implantation driver 500 can have a driver head 541 configured to selectively engage corresponding receptacle 542 in the head of attachment device 532. Driver head 541 can further comprise a locking pin 543 configured to releasably engage a corresponding receiver in the side wall of receptacle 542, thereby securing the assembled distractor cam device to the implantation driver. Implantation driver 500 can further feature lateral pins 544 configured to be received by implantation driver slots 535. The interface between lateral pins 544 and fixation plate 530 at implantation driver slots 535 can provide for enhanced torque transfer from implantation driver 500 to assembled implantable distractor cam device 540 for actuation of the distractor cam and distraction of the gap while minimizing risk of over-engagement or stripping of attachment device 532 in the distractor cam, or loosening of attachment device 532 from the distractor cam with rotation in the opposite direction. In various embodiments, implantation driver can be released from the implanted distractor cam device 540 by operator actuation of locking pin 543, such as with a button or lever located on the handle of implantation driver 500, disengagement of a threaded screw, or any other device which may be used to attach the driver to the implantable distractor cam device.

Implantation driver 600 illustrated in FIG. 6 includes similar features to implantation driver 500. However, implantation driver 600 is configured to engage distractor cam 631 directly. Driver head 641 may be configured to engage a receptacle in distractor cam 631 such as a threaded insert or tapped hole 645 that may later be used to receive an attachment device for securing a fixation plate to distractor cam 631. Distractor cam 631 may include sockets 646 configured to receive lateral pins 644. In the illustrated embodiment with a cylindrical driver head 641 and tapped hole 645, the interface between the sockets and lateral pins may provide for substantially all of the torque transfer from implantation driver 600 to distractor cam 631. In various embodiments, other interfaces and retention mechanisms, such as slots or other non-round driver shapes or configurations (e.g., torx, cross, hex, etc.) may be used between an implantation driver and an assembled implantable distraction device or a distractor cam.

Figure 7A:
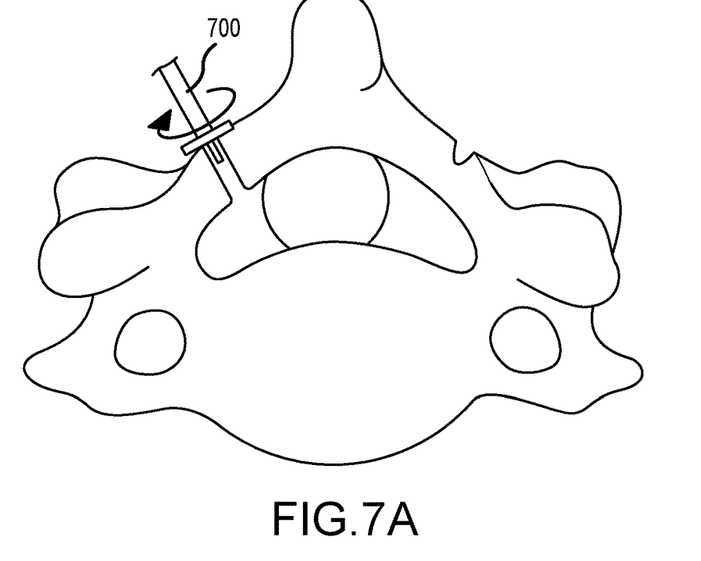
FIGS. 7A and 7B illustrates a portion of a distraction procedure using a distraction driver in accordance with various embodiments of the present disclosure.
Figure 7B:
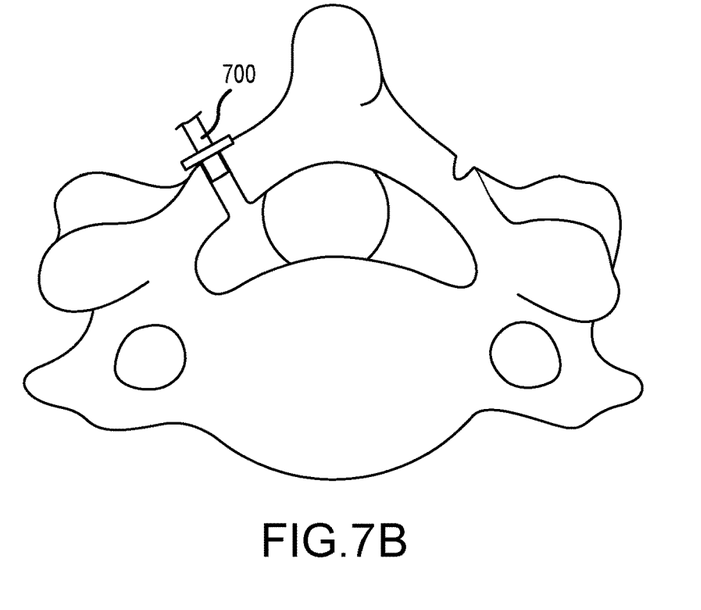

In various embodiments, a method of implanting an osteodistraction device is provided, for example, in connection with what is known to those skilled in the art as "open door" or "French door" laminoplasty procedures. A method can comprise inserting a distal end of a distraction driver 700 into a gap having a gap dimension between a first bone surface and a second bone surface (FIGS. 7A and 7B). The distraction driver can be inserted into the gap until a distal surface of a protection plate contacts a surface of the bone structure. The method can further comprise rotating the distraction driver in a first direction about a longitudinal axis to produce a distraction force (i.e., by controlled distraction) on the first bone surface and the second bone surface. The amount of rotation can be about 90 degrees, or more or less than 90 degrees based on the particular application and/or the desired distraction. The distraction force can produce linear displacement of the first bone surface and the second bone surface to produce a first distracted gap dimension between the bone structures. The first distracted gap dimension may be greater than the gap dimension and may approximately correspond to a second cam dimension. The method can further comprise further rotating the distraction driver in one of the first direction or a second direction opposite the first direction to controllably reduce the distraction force on the first bone surface and the second bone surface. The method can further comprise removing the distal end of the distraction driver following controllably reducing the distraction force.

As used herein, "controlled distraction" means producing displacement of two surfaces or structures by means of a mechanical device that maintains contact with both surfaces or structures throughout the distraction process and relies on forces and movements substantially parallel to the direction of displacement, such as the rotational movement and forces of a disk cam device inserted between two surfaces to be displaced from one another by rotation of the disk cam. A distraction device suitable to provide controlled distraction in accordance with various embodiments described and illustrated herein minimizes risk of slipping during engagement and operation of the device, and further minimizes the risk of an abrupt loss of distraction due to insertion into the gap between surfaces to be distracted and the manner in which the device fully occupies the gap. In contrast, a simple lever, forceps, spreader or other device may include techniques, forces and directions of movement associated with an increased risk of slippage and/or an abrupt return of the displaced structures to an undistracted position. Such an abrupt return of the displaced structures may produce undesirable consequences.

In various embodiments, sequential controlled distraction may be performed using a plurality of distraction drivers comprising distraction cams with increasing distraction dimensions. Sequential controlled distraction may produce progressive increases in the distracted gap dimension. This sequential controlled distraction can comprise a predistraction process to prepare for final distraction using an assembled implantable distraction device in accordance with various embodiments.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. A modular system for osteodistraction comprising:
a distraction component comprising a body with cross-section, the body having a first dimension, a second dimension greater than the first dimension, and a third dimension;
a fixation component configured to be adjustably coupled to the distraction component;
an attachment component configured to adjustably couple the distraction component and the fixation component, wherein adjustment of the attachment component adjusts the relative position of the distraction component and the fixation component; and
an insertion component, wherein the insertion component comprises an elongated shaft with a proximal end and a distal end, wherein the distal end is configured to positively secure and reversibly engage a head of the attachment component.

2. The modular system of claim 1, wherein the cross-section is substantially symmetrical about one of an axis in the first dimension and an axis in the second dimension.

3. The modular system of claim 2, wherein the cross-section comprises a convexly curved profile along a substantial length of distraction component surfaces defining the cross-section in the second dimension.

4. The modular system of claim 3, wherein the cross-section provides for translation of adjacent bone surfaces in a direction substantially perpendicular to the axis of rotation of the distraction component.

5. The modular system of claim 1, wherein the fixation component comprises a surface feature configured to engage a surface of the distraction component.

6. The modular system of claim 1, wherein rotation of the attachment component rotates the distraction component relative to the fixation component.

7. The modular system of claim 1, wherein a driver head of the insertion component corresponds to, and is configured to positively secure and reversibly engage, a receptacle in the head of the attachment component.

8. A kit for performing a distraction and implanting a distractor cam device comprising:
a plurality of distraction drivers, each of the plurality of distraction drivers comprising:
an elongated shaft with a distal distraction driver end and a proximal distraction driver end;
a distraction cam at the distal distraction driver end, the distraction cam comprising an insertion dimension and a distraction dimension; and
a protective plate comprising a diameter dimension greater than the distraction dimension;
wherein the plurality of distraction drivers is configured to progressively increasing distraction dimensions;
an implantable distractor cam device comprising:
a distractor cam;
a fixation plate; and
an attachment device;
wherein the fixation plate is configured to be adjustably coupled to the distractor cam using the attachment device to produce an assembled implantable distractor cam device; and
an implantation driver comprising an elongate shaft with a distal end and a proximal end, wherein the implantation driver is configured to reversibly engage the assembled implantable distractor cam device.

9. The kit of claim 8, further comprising a plurality of operator-selectable fixation plates, the plurality of operator-selectable fixation plates providing at least one of a range of different fixation plate lengths or a range of different fixation plate configurations.

10. The kit of claim 8, further comprising plurality of operator-selectable distractor cams.

11. The kit of claim 8, wherein the plurality of distraction drivers comprises a set of three distraction drivers configured to provide a distraction dimension delta of at least about 4 mm.

12. The kit of claim 8, wherein the plurality of distraction drivers is configured to provide distraction dimensions of between about 2 mm and about 20 mm.

13. A method of implanting an osteodistraction device comprising:
inserting a distal end of a distraction driver into a gap having a gap dimension between a first bone surface and a second bone surface, wherein the distraction driver comprises a distraction cam at the distal end, the distraction cam having a first cam dimension and a second cam dimension greater than the first dimension;

wherein the distraction driver is inserted into the gap until a surface of a protection plate contacts a surface of the bone structure;

rotating the distraction driver in a first direction about a longitudinal axis to produce a distraction force on the first bone surface and the second bone surface, wherein the distraction force produces displacement of the first bone surface and the second bone surface, and wherein the displacement produces a first distracted gap dimension between the bone structures, wherein the first distracted gap dimension is greater than the gap dimension and wherein first distracted gap dimension approximately corresponds to the second cam dimension;

further rotating the distraction driver in one of the first direction or a second direction opposite the first direction to controllably reduce the distraction force on the first bone surface and the second bone surface; and removing the distal end of the distraction driver from the gap.

14. The method of claim 13, wherein controllably reducing the distraction force and removing the distal end of the distraction driver does not produce an abrupt movement of either of the first bone surface and the second bone surface.

15. The method of claim 14, further comprising performing sequential predistraction steps to produce progressive increases in the distracted gap dimension.

16. The method of claim 13, further comprising implanting an assembled implantable distractor cam device.

17. The method of claim 13, further comprising implanting a distractor cam followed by attachment of a fixation plate to the distractor cam.

* * * * *